(12) United States Patent
Parida et al.

(10) Patent No.: US 7,622,636 B2
(45) Date of Patent: Nov. 24, 2009

(54) **DEHYDRIN GENE FROM *AVICENNIA MARINA* RESPONSIBLE FOR CONFERRING SALT TOLERANCE IN PLANTS**

(75) Inventors: Ajay Parida, Chennai (IN); Preeti Mehta Angela, Chennai (IN); Gayatri Venkatraman, Chennai (IN)

(73) Assignee: M.S. Swaminathan Research Foundation, Chennai (IN)

( * ) Notice: Subject to any disclaimer, the term of this patent is extended or adjusted under 35 U.S.C. 154(b) by 0 days.

(21) Appl. No.: 11/997,725

(22) PCT Filed: Jul. 31, 2006

(86) PCT No.: PCT/IN2006/000270

§ 371 (c)(1),
(2), (4) Date: Jul. 16, 2008

(87) PCT Pub. No.: WO2007/015267

PCT Pub. Date: Feb. 8, 2007

(65) Prior Publication Data

US 2008/0307538 A1 Dec. 11, 2008

(30) Foreign Application Priority Data

Aug. 3, 2005 (IN) .................. 1050/CHE/2005

(51) Int. Cl.
*A01H 5/00* (2006.01)
*C12N 15/82* (2006.01)
*C12N 15/87* (2006.01)
*C12N 5/14* (2006.01)
*C12N 15/63* (2006.01)
*C07H 21/00* (2006.01)

(52) U.S. Cl. .............. 800/295; 800/278; 800/306; 800/312; 800/317.4; 800/320; 800/320.1; 800/320.2; 435/468; 435/419; 536/23.1; 536/23.6; 536/24.1

(58) Field of Classification Search .............. None
See application file for complete search history.

(56) References Cited

U.S. PATENT DOCUMENTS 5,981,842 A * 11/1999 Wu et al. .................. 800/298
2002/0160378 A1* 10/2002 Harper et al. .................. 435/6

FOREIGN PATENT DOCUMENTS

WO    WO 02090547 A1 * 11/2002

OTHER PUBLICATIONS

Kasuga et al. (Plant Cell Physiology, 45:346-350, 2004).*
Kasuga et al. (NCBI, GenBank Sequence Accession No. AB049336. 1, Published Mar. 31, 2004).*

* cited by examiner

*Primary Examiner*—Vinod Kumar
(74) *Attorney, Agent, or Firm*—Lowe Hauptman Ham & Berner, LLP

(57) ABSTRACT

The present invention relates to a method of producing salt-stress tolerant plants by transforming the plants with an isolated nucleic acid sequences encoding a dehydrin (DHN) protein. The invention further provides a transgenic plant expressing the dehydrin gene of *Avicennia marina*. Using functional genomics, this gene was derived from large-scale EST sequencing of the cDNA library of the salt tolerant mangrove *Avicennia marina*.

14 Claims, 2 Drawing Sheets

SEQUENCE LISTING

```
<160> NUMBER OF SEQ ID NOS: 16

<210> SEQ ID NO 1
<211> LENGTH: 1026
<212> TYPE: DNA
<213> ORGANISM: Avicienna marina

<400> SEQUENCE: 1
cggacgcgtg gggtgtatct cgtatttcag atatctttaa gctcagagaa tatggcagag      60
tacggcgacc aatacgggcg acagaccgac gagtatggca atcccatccg ccagactggt     120
gagtttggag ctaccggggc ttacggggct aatcagcagt atgaaccac cggcaccacc     180
```

-continued

```
gtagggtatg ggactgatca gtgtgtcacc accgtcacga ccggggctca agactgac      240 cagtatggaa ccccggcac gaccggagca tatgggactg atcagtatgg aaccaccggc      300
accaccgggg aatatgggac cacggtggt gggattgctc caggagcaac tgatgctggc      360
ctagctggcg gcggcggagg ccaccgccgc ttgggcagct caggcagctc ggtatgtgac      420
tataaattaa actttacctg ttcattttgc tttcccgtat gcatgtgatg actaattcca      480
ggattacgat tttttatttc ctccatgaat ggcagtcctc agaggacgac gggcaaggtg      540
ggaggagaaa aagggggata aaggagaaga taaagagaa gctacccggc ggcggtcacg      600
gggatgatca gactcacccc actccacctg gcagcggcgg atatggttat gagcacgggg      660
gagcggccga agcccagag catgaagaga agaagggaat aatggataag ataaaggaaa      720
agctgcccgg cggccaccat taagtataac tgtatacaag aacaagggga tgtttgtatc      780
aaacatcatc attaagttta ttgatcttgc tagatgaagc atatacacat tatacacaat      840
aagccattct cagctttatc acaatctgag aagggcacgc gaatgtcagt ttgggtactt      900
ataattgttg cttttccagc tacttgtgtt tgggtgtaat ccgtttctgt attataaatt      960
gttgtatgat atgtaattaa tgcgtatata tgaatgaata cttttgtgtt aaaaaaaaaa     1020
aaaaaa                                                                1026

<210> SEQ ID NO 2
<211> LENGTH: 588
<212> TYPE: DNA
<213> ORGANISM: Artificial
<220> FEATURE:
<223> OTHER INFORMATION: Synthetic sequence

<400> SEQUENCE: 2
atggcagagt acggcgacca atacgggcga cagaccgacg agtatggcaa tcccatccgc       60
cagactggtg agtttggagc taccgggggct tacggggcta atcagcagta tggaaccacc      120
ggcaccaccg tagggtatgg gactgatcag tgtgtcacca ccgtcacgac cggggctcag      180
aagactgacc agtatggaac ccccggcacg accggagcat atgggactga tcagtatgga      240
accaccggca ccaccgggga atatgggacc cacggtggtg ggattgctcc aggagcaact      300
gatgctggcc tagctggcgg cggcggaggc caccgccgct tgggcagctc aggcagctcg      360
tcctcagagg acgacgggca aggtgggagg agaaagaagg ggataaagga agataaaa        420 gagaagctac ccggcggcgg tcacggggat gatcagactc accccactcc acctggcagc      480
ggcggatatg gttatgagca cggggagcg gccgaaagcc cagagcatga agaagaag        540 ggaataatgg ataagataaa ggaaaagctg cccggcggcc accattaa                    588

<210> SEQ ID NO 3
<211> LENGTH: 249
<212> TYPE: PRT
<213> ORGANISM: Avicennia marina

<400> SEQUENCE: 3

Met Ala Glu Tyr Gly Asp Gln Tyr Gly Arg Gln Thr Asp Glu Tyr Gly
1               5                   10                  15

Asn Pro Ile Arg Gln Thr Gly Glu Phe Gly Ala Thr Gly Ala Tyr Gly
            20                  25                  30

Ala Asn Gln Gln Tyr Gly Thr Thr Gly Thr Thr Val Gly Tyr Gly Thr
        35                  40                  45

Asp Gln Cys Val Thr Thr Val Thr Thr Gly Ala Gln Lys Thr Asp Gln
    50                  55                  60
```

```
Tyr Gly Thr Pro Gly Thr Gly Ala Tyr Gly Thr Asp Gln Tyr Gly
 65                  70                  75                  80

Thr Thr Gly Thr Thr Gly Glu Tyr Gly Thr His Gly Gly Gly Ile Ala
                 85                  90                  95

Pro Gly Ala Thr Asp Ala Gly Leu Ala Gly Gly Gly Gly His Arg
            100                 105                 110

Arg Leu Gly Ser Ser Gly Ser Ser Val Cys Asp Tyr Lys Leu Asn Phe
            115                 120                 125

Thr Cys Ser Phe Cys Phe Pro Val Cys Met Cys Ala Asn Ser Arg Ile
        130                 135                 140

Thr Ile Phe Tyr Phe Leu His Glu Trp Gln Ser Ser Glu Asp Asp Gly
145                 150                 155                 160

Gln Gly Arg Arg Lys Lys Gly Ile Lys Glu Lys Ile Lys Glu Lys
            165                 170                 175

Leu Pro Gly Gly Gly His Gly Asp Asp Gln Thr His Pro Thr Pro Pro
                180                 185                 190

Gly Ser Gly Gly Tyr Gly Tyr Glu His Gly Gly Ala Ala Glu Ser Pro
            195                 200                 205

Glu His Glu Glu Lys Lys Gly Ile Met Asp Lys Ile Lys Glu Lys Ala
            210                 215                 220

Ala Glu Ser Pro Glu His Glu Glu Lys Lys Gly Ile Met Asp Lys Ile
225                 230                 235                 240

Lys Glu Lys Leu Pro Gly Gly His His
                245

<210> SEQ ID NO 4
<211> LENGTH: 793
<212> TYPE: DNA
<213> ORGANISM: Avicennia marina

<400> SEQUENCE: 4
ggtcgagtga aagaataggg ttgtgaatat ggtggtcgag tgagatgaag tgatggtatg    60
agccaaatgg gccagccata gaagtgccta aattgtttgg gacaatgata cattcatagt   120
gggtgacacc tgtgaggccc aaattgacca atgcatgtag attctaccat atcatgccag   180
gtgaccacca taatcatca tccatcatca gttattggtt ccttcttcac cttaacttgt    240
cttgcaaccg acaacttcgc cttttcccaa cggtcaactt tgtcatacc caaataacca    300 tcgcttcatc tgtatacgtg gctctgcgtt gatcacatca caatcgacaa gtgtcatatc   360
tctccgagac taatgcatgt atggatccaa tctaaataaa ctagataagc ttttcagtaa   420
cgtgtgatta taaaattccg tggattcaaa ctttaccgaa aattttaagt tgaattccat   480
tcatgtatat cttctgagtt ggactttagt ttatcattct gtgggtttat ccacatttgc   540
cgacaacgga cacctgtcca aatcttgctg gagatgtgga acccaagatc ccaacgtggc   600
atctgcataa tttattgcat gcaacacctg cgagttttcc ctgtcatccg ctttcgagac   660
tgcgcatccc ttgcattcta tatatatatc cccccccccg catggcagta accattgca    720 tcagttcgta gaactatcat tttcagtgta tctcgtattt cagaaatctt taagctcaga   780
gaatatggca gag                                                      793

<210> SEQ ID NO 5
<211> LENGTH: 26
<212> TYPE: DNA
<213> ORGANISM: Artificial
<220> FEATURE:
<223> OTHER INFORMATION: Synthetic sequence
```

```
<400> SEQUENCE: 5
gctctagaat ggcagagtac ggcgac                                            26

<210> SEQ ID NO 6
<211> LENGTH: 25
<212> TYPE: DNA
<213> ORGANISM: Artificial
<220> FEATURE:
<223> OTHER INFORMATION: Synthetic sequence

<400> SEQUENCE: 6
ccgctcgagt taatggtggc cgccg                                             25

<210> SEQ ID NO 7
<211> LENGTH: 23
<212> TYPE: DNA
<213> ORGANISM: Artificial
<220> FEATURE:
<223> OTHER INFORMATION: Synthetic sequence

<400> SEQUENCE: 7
tacggtggtg ccggtggttc cat                                               23

<210> SEQ ID NO 8
<211> LENGTH: 24
<212> TYPE: DNA
<213> ORGANISM: Artificial
<220> FEATURE:
<223> OTHER INFORMATION: Synthetic sequene

<400> SEQUENCE: 8
tgggattgcc atactcgtcg gtct                                              24

<210> SEQ ID NO 9
<211> LENGTH: 26
<212> TYPE: DNA
<213> ORGANISM: Artificial
<220> FEATURE:
<223> OTHER INFORMATION: Synthetic sequence

<400> SEQUENCE: 9
ctctgccata ttctctgagc ttaaag                                            26

<210> SEQ ID NO 10
<211> LENGTH: 16
<212> TYPE: DNA
<213> ORGANISM: Artificial
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 10
ngtcgaswga nawgaa                                                       16

<210> SEQ ID NO 11
<211> LENGTH: 16
<212> TYPE: DNA
<213> ORGANISM: Artificial
<220> FEATURE:
<223> OTHER INFORMATION: Synthetic Sequence
```

```
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 11
tgwgnagsan casaga                                                      16

<210> SEQ ID NO 12
<211> LENGTH: 16
<212> TYPE: DNA
<213> ORGANISM: Artificial
<220> FEATURE:
<223> OTHER INFORMATION: Synthetic sequence
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 12
wgtgnagwan canaga                                                      16

<210> SEQ ID NO 13
<211> LENGTH: 16
<212> TYPE: DNA
<213> ORGANISM: Artificial
<220> FEATURE:
<223> OTHER INFORMATION: Synthetic Sequence
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 13
sttgntastn ctntgc                                                      16

<210> SEQ ID NO 14
<211> LENGTH: 22
<212> TYPE: DNA
<213> ORGANISM: Artificial
<220> FEATURE:
<223> OTHER INFORMATION: Synthetic sequence

<400> SEQUENCE: 14
ggagagatat gacacttgtc ga                                               22

<210> SEQ ID NO 15
<211> LENGTH: 22
<212> TYPE: DNA
<213> ORGANISM: Artificial
```

-continued

```
<220> FEATURE:
<223> OTHER INFORMATION: Synthetic Sequence

<400> SEQUENCE: 15
gtcggttgca agacaagtta ag                                              22

<210> SEQ ID NO 16
<211> LENGTH: 23
<212> TYPE: DNA
<213> ORGANISM: Artificial
<220> FEATURE:
<223> OTHER INFORMATION: Synthetic Sequence

<400> SEQUENCE: 16
cacccactat gaatgtatca ttg                                             23
```

DEHYDRIN GENE FROM *AVICENNIA MARINA* RESPONSIBLE FOR CONFERRING SALT TOLERANCE IN PLANTS

RELATED APPLICATIONS

The present application is based on International application number PCT/IN2006/000270 filed Jul. 31, 2006, and claims priority from Indian Application Number 1050/CHE/2005 filed Aug. 3, 2005, the disclosures of which are hereby incorporated by reference herein in their entirety.

FIELD OF INVENTION

The present invention relates to the field of plant molecular biology, particularly to transgenic plants which comprises the nucleic acid encoding a late embryogenesis abundant protein which confers salt-stress tolerance in plants.

BACKGROUND OF THE INVENTION

Partial sequencing of anonymous cDNA clones (Expressed Sequence Tags, ESTs) is a rapid and cost effective method for the generation of data on coding capacity of genomes. In plants, this method was first used for *Arabidopsis thaliana* and *Oryza sativa* (Höfte et al. 1993; Cooke et al. 1996; Rounsley et al. 1996; Yamamoto et al. 1997). It has subsequently been used for many other plant species such as *Medicago, Mesembryanthemum*, wheat, barley, tomato, potato, pine and sunflower (Györgyey et al. 2000; Ozturk et al. 2002; Van der Hoeven et al. 2002; Ronning et al. 2003 Allona et al. 1998). This abundance of sequence information presents opportunities to accelerate progress towards understanding genetic mechanisms that control plant growth and responses to the environment. Environmental factors such as drought, extreme temperatures, high or fluctuating salinity can affect plant growth and performance and in the case of agronomically important plants, this may translate to reduced yield. In particular, increasing soil salinisation in irrigated areas has necessitated the identification of crop traits/genes which confer resistance to salinity (Cushman and Bohnert 2000).

Hyperosmotic stress, such as that caused by exposure of cells to high concentrations of NaCl causes imbalance of cellular ions, change in turgor pressure and cell volume and alters the activity and stability of macromolecules. Characterization and cloning of plant genes that confer salinity tolerance remains a challenge. Genetic studies revealed that tolerance to drought and salinity in some crop varieties is principally due to additive gene effects. Physiological and biochemical responses to high levels of ionic or nonionic solutes and decreased water potential have been studied in a variety of plants. Based on accumulated experimental observations and theoretical consideration, one suggested mechanism that may underlie the adaptation or tolerance of plants to osmotic stresses is the accumulation of compatible, low molecular weight osmolytes such as sugar alcohols, special amino acids and glycinebetaine (Greenway and Munns, 1980). In addition to metabolic changes and accumulation of low molecular weight compounds, a large set of genes is transcriptionally activated which leads to accumulation of new proteins in vegetative tissue of plants under osmotic stress conditions (Skriver and Mundy, 1990).

SUMMARY OF INVENTION

The present invention relates to the nucleic acid sequences encoding a dehydrin protein derived from *Avicennia marina*, responsible for conferring salt stress tolerance. The invention also relates to a method of isolating unique transcripts from *Avicennia marina* conferring salt tolerance, comprising steps critical for enhanced expression of said transcripts. Further, the invention provides a method for producing a transgenic plant comprising the dehydrin gene form *A. marina*. The invention also relates to a salt tolerant transgenic plant expressing said gene.

One aspect of the invention relates to an isolated polynucleotide sequence comprising at least 80% similarity to SEQ ID NO: 1 coding for dehydrin protein having amino acid sequence as shown in SEQ ID NO: 3.

Another aspect of the invention relates to a recombinant construct for transforming plants to confer salt stress tolerance, wherein said construct comprising regulatory sequence operably linked to a polynucleotide sequence as shown in SEQ ID NO: 1, or a fragment or a variant thereof.

Yet another aspect of the invention relates to an isolated promoter functional in plant cells comprising:
a. a polynucleotide sequence set forth in SEQ ID NO: 4, or
b. a polynucleotide sequence having at least 200 contiguous nucleotides of the polynucleotide sequence as set forth in SEQ ID NO: 4.

Still another aspect of the invention relates to a recombinant vector comprising the promoter operably linked to a heterologous DNA sequence of interest.

Yet another aspect of the invention relates to a method of plant transformation to confer salt stress tolerance in a plant, said method comprising transforming a plant with a recombinant vector comprising a regulatory sequence operably linked to the polynucleotide sequence comprising at least 80% similarity to SEQ ID NO: 1 coding for dehydrin protein having amino acid sequence as shown in SEQ ID NO: 3 to produce salt stress tolerant plant.

Yet another aspect of the invention relates to a transgenic plant transformed with the polynucleotide sequence comprising at least 80% similarity to SEQ ID NO: 1 coding for dehydrin polypeptide having amino acid sequence as shown in SEQ ID NO: 3.

Still another aspect of the invention relates to a plant, a plant part, a seed, a plant cell and a progeny thereof, wherein the plant, plant part, seed, plant cell, or progeny thereof comprises the recombinant construct.

DETAILED DESCRIPTION OF THE INVENTION

Figure 1:
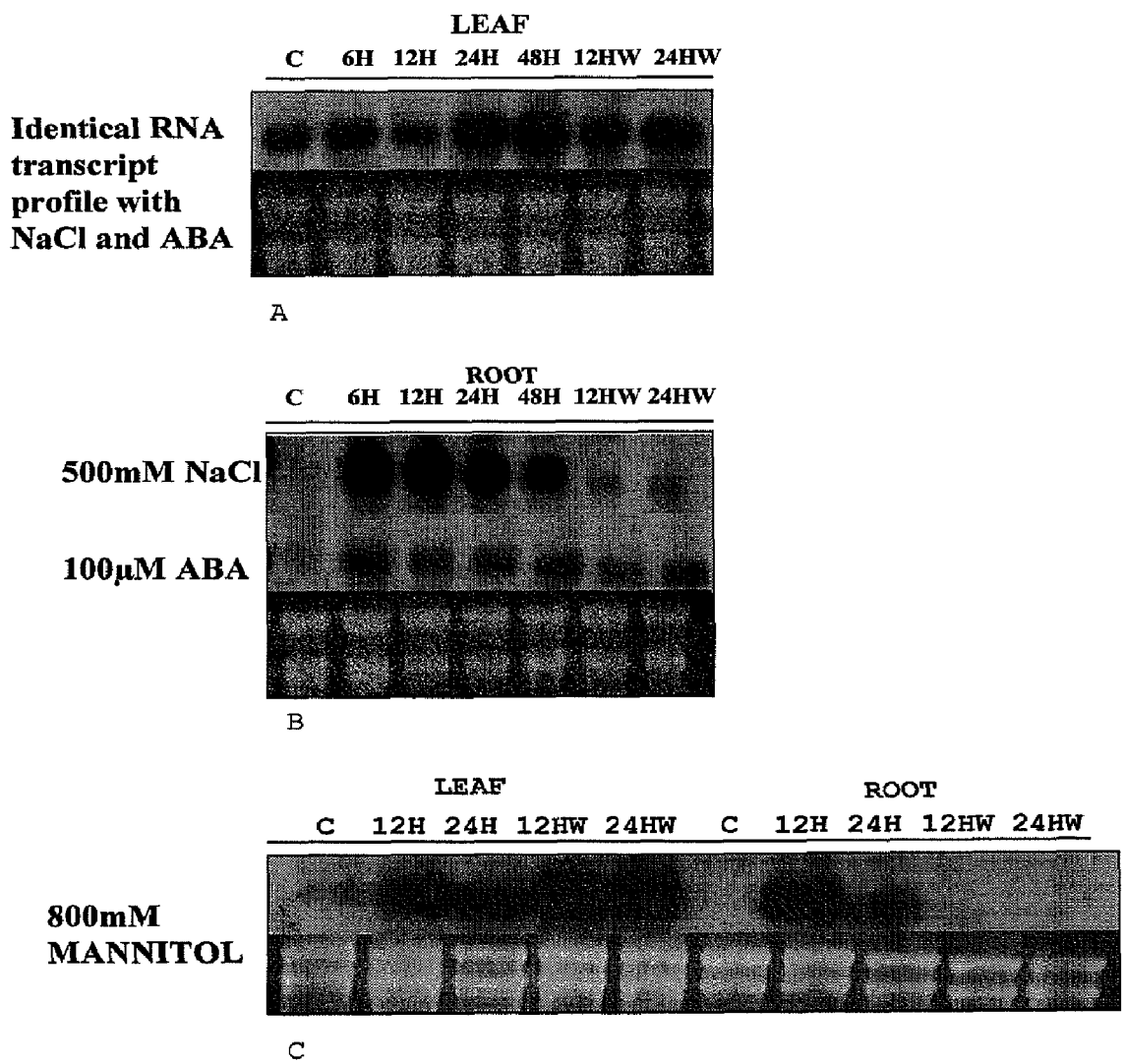
FIG. 1: Northern analysis on leaf and root tissues of *Avicennia marina* seedlings grown under stress (NaCl, ABA and mannitol) as indicated in the figure. A. Leaf tissue; B. Root tissue; and C. Leaf and root tissues. C represents control. Tissues were frozen at 6 H (6 hours), 12 H (12 hours), 24 H (24 hours), and 48 H (48 hours) after stress treatment. Tissues were frozen at 12 HW (12 hours after stress withdrawal) and 24 HW (24 hours after stress withdrawal).

The present invention relates to the nucleic acid sequences encoding the dehydrin protein derived from *Avicennia marina*, responsible for conferring salt stress tolerance. The invention also relates to a method of isolating unique transcripts from *Avicennia marina* conferring salt tolerance, comprising steps critical for enhanced expression of said transcripts. The invention also relates to a salt tolerant transgenic plant which expresses said gene. Further, the invention provides a method for producing a transgenic plant expressing said gene product.

An embodiment of the present invention relates to an isolated polynucleotide sequence comprising at least 80% similarity to SEQ ID NO: 1 coding for dehydrin protein having amino acid sequence as shown in SEQ ID NO: 3.

Another embodiment of the present invention relates to a recombinant construct for transforming plants to confer salt stress tolerance, wherein said construct comprising regulatory sequence operably linked to a polynucleotide sequence as shown in SEQ ID NO: 1, or a fragment or a variant thereof.

Yet another embodiment of the present invention relates to a recombinant construct, wherein said regulatory sequence is selected from a group consisting of 35S CaMV promoter, nopaline synthase promoter, OCS, AdhI, AdhII, native promoter of DHN gene and Ubi-1.

Yet another embodiment of the present invention relates to an isolated promoter functional in plant cells comprising:
 a. a polynucleotide sequence set forth in SEQ ID NO: 4, or
 b. a polynucleotide sequence having at least 200 contiguous nucleotides of the polynucleotide sequence as set forth in SEQ ID NO: 4.

Still another aspect the present invention relates to a recombinant vector comprising the promoter having polynucleotide sequence as shown in SEQ ID NO: 4 or a polynucleotide sequence having at least 200 contiguous nucleotides of the polynucleotide sequence as set forth in SEQ ID NO: 4 operably linked to a heterologous DNA sequence of interest.

Yet another aspect the present invention relates to the recombinant vector, wherein the heterologous DNA sequence encodes a protein selected from a group consisting of insect resistance protein, a bacterial disease resistance protein, a fungal disease resistance protein, a viral disease resistance protein, a nematode disease resistance protein, a herbicide resistance protein, a protein affecting grain composition or quality, a selectable marker protein, a screenable marker protein, a protein affecting plant agronomic characteristics, and a stress resistance protein.

Still yet another embodiment of the present invention relates to a method of transformation of plants to confer salt stress tolerance in a plant, said method comprising transforming a plant with a recombinant vector comprising a regulatory sequence operably linked to the polynucleotide sequence comprising at least 80% similarity to SEQ ID NO: 1 coding for dehydrin protein having amino acid sequence as shown in SEQ ID NO: 3 to produce salt stress tolerant plant.

In a preferred embodiment the plant transformation is carried out by a method selected from a group consisting of *Agrobacterium*-mediated transformation, particle gun bombardment, vacuum-infiltration, in planta transformation and chemical methods.

In yet another embodiment *Agrobacterium*-mediated transformation method comprises:
 a. constructing a recombinant construct,
 b. mobilizing the recombinant construct of step (a) into *Agrobacterium* strain to produce recombinant *Agrobacterium* strains,
 c. obtaining a suitable explant from the plant,
 d. cultivating the explant with the recombinant *Agrobacterium* strain of step (b) to produce transformed plant cells,
 e. culturing the transformed plant cells to produce transformed plants,
 f. obtaining transformed plants.

The present invention relates to monocotyledonous or a dicotyledonous plant transformation, wherein the plant is selected from a group consisting of rice, maize, wheat, barley, sorghum, tobacco, tomato, pea, soybean, *brassicas*, peanut, chickpea and pigeon pea.

One embodiment provides *Agrobacterium* strain selected from a group consisting of LBA4404, EHA101 and EHA105.

Another embodiment provides explant selected from a group consisting of leaf, stem, root, hypocotyl and embryo.

Yet another embodiment provides a transformed plant cell comprising polynucleotide sequence as shown in SEQ ID NO: 1 or a fragment or a variant thereof.

Still another embodiment provides a transgenic plant transformed with the polynucleotide sequence comprising at least 80% similarity to SEQ ID NO: 1 coding for dehydrin polypeptide having amino acid sequence as shown in SEQ ID NO: 3.

Another embodiment provides the transgenic plant selected from a group consisting of tobacco, tomato, pea, soybean, *Brassica*, chickpea, pigeon pea, rice, maize, wheat, barley and sorghum.

Yet another embodiment provides a plant, a plant part, a seed, a plant cell and a progeny thereof, wherein the plant, plant part, seed, plant cell, or progeny thereof comprises the recombinant construct.

The invention provides a cDNA sequence (SEQ ID NO: 2) from *A. marina* and a protein encoded by said cDNA sequence. The nucleotide sequence for the gene which codes for dehydrin is as shown in SEQ ID NO: 1 and is illustrative of a sequence encompassed by the present invention. The protein encoded by this gene is as shown in SEQ ID NO: 3. The sequence encoding DHN (SEQ ID NO: 1), as well as sequences derived therefrom, also provide probes useful for isolation of genes and related genes from other organisms. The invention also relates to a salt tolerant transgenic plant which expresses said gene and a method for producing a transgenic plant expressing said gene product involving isolating the DHN cDNA from total mRNA from leaf of one month old salt challenged *A. marina* seedlings, cloning it in a plant transformation vector as an expression cassette (pDHN1), in a manner that the cDNA encoding DHN is operably linked to 35S CaMV promoter and nopaline synthase. The plant transformation vector additionally contains reporter gene cassette and an antibiotic selection cassette for the selection of transgenic plants. The present invention also relates to *Agrobacterium* mediated plant transformation method to produce salt tolerant plant comprising the polynucleotide sequence encoding DHN protein of *A. marina*. The present invention also relates to a method of isolating unique transcripts from conferring salt tolerant properties comprising steps critical for enhanced expression of the transcripts.

The present invention relates to the nucleic acid sequences encoding a novel unknown protein bearing similarity to a putative phytosulfokine peptide precursor, derived from *Avicennia marina*, responsible for conferring salt stress tolerance.

The invention also relates to a method of isolating unique transcripts from *Avicennia marina* conferring salt tolerance, comprising steps critical for enhanced expression of said transcripts.

A preferred embodiment of the present invention relates to isolation of DHN cDNA from *Avicennia marina*. Total RNA was isolated from leaf tissues of one month old *Avicennia marina* seedlings that had been treated with NaCl 48 h before harvesting. These conditions were critical for induction of the DHN transcripts to levels that allowed their cloning as cDNA inserts in a cDNA library. Total RNA was isolated from leaf tissues of salt stressed plants according to Chomczynski and Sacchi (1987). Total mRNA can also be extracted using methods well known in the art. The present invention also relates to the kinetics of induction of AmDHN, one month old *A. marina* seedlings were acclimatized for 72 hours in 0.5×MS nutrient solution and then exposed to salt stress, osmotic stress and ABA treatment. Root and leaf tissue were frozen separately for total RNA isolation. The details on growth conditions and the protocol followed for RNA isolation are provided in Example 1.

The present invention also relates to the construction of cDNA library using *A. marina* RNA isolated in the above description. cDNA prepared from poly (A+) mRNA was size fractionated over SizeSep-400 spun column and directionally cloned in the Sal I (5')/Not I (3') sites of pSPORT1. The methods for cDNA synthesis known in the art involve using poly (A+) RNA as a template for reverse transcription employing an oligo (dT) primer and a reverse transcriptase enzyme to synthesize first strand cDNA. These methods for synthesis of cDNA and cloning in suitable vectors are well known in art. For experimental details, see Example 2.

The present invention relates to the sequencing of the identified clone carrying AmDHN cDNA as an insert. The complete nucleic acid sequence of both strands of the full length cDNA was determined using the dideoxy chain termination method (Sanger et al., 1977) using M13/pUC18 forward and reverse primers. This cDNA insert was subcloned into pBluescript SK vector at the Pst I (5')/Hind III (3') sites. This recombinant clone is designated as pDHN1. The insert in pDHN1 was sequenced confirmed. The nucleic acid and protein sequence is as shown in SEQ ID NO: 2 and SEQ ID NO: 3.

The complete coding region was isolated by one-step reverse transciptase-polymerase chain reaction (RT-PCR) from messenger RNA (mRNA) isolated from roots of *A. marina* exposed to 12 h of 0.5M NaCl stress. The primers PC57 FWD 2 (SEQ ID NO: 5) and PC57 REV1 (SEQ ID NO: 6) were used. The methodological aspects of sequence analysis are discussed in Example 3. Equal amounts of total RNA (30 µg) were electrophoresed on a 1.2% MOPS-formaldehyde gel, transferred to nylon membrane and fixed by UV cross-linking. The membrane was hybridized with the probe and results are given in FIG. 1.

```
PC57 FWD2:
5'-GCTCTAGAATGGCAGAGTACGGCGAC-3'    SEQ ID NO: 5

PC57 REV1:
5'-CCGCTCGAGTTAATGGTGGCCGCCG-3'     SEQ ID NO: 6
```

In yet another embodiment, the present invention relates to checking the expression of AmDHN protein in prokaryotic system. The cDNA of AmDHN (SEQ ID NO: 2) was amplified using gene-specific primers containing restriction sites for facilitating cloning. The amplified fragment was double digested with Xba I and Xho I and directionally cloned into the Nhe I and Xho I sites of vector pET28a *E. coli* expression vector. The cloned insert was confirmed by automated DNA sequencing using the universal primers. Example 4 gives the details on the methodology followed for constructing the protein expression vector. Protein extraction and quantification were done by methods well known in the art. Subsequently, western blotting was carried out. For details of the experiments please refer Example 5.

Figure 2:
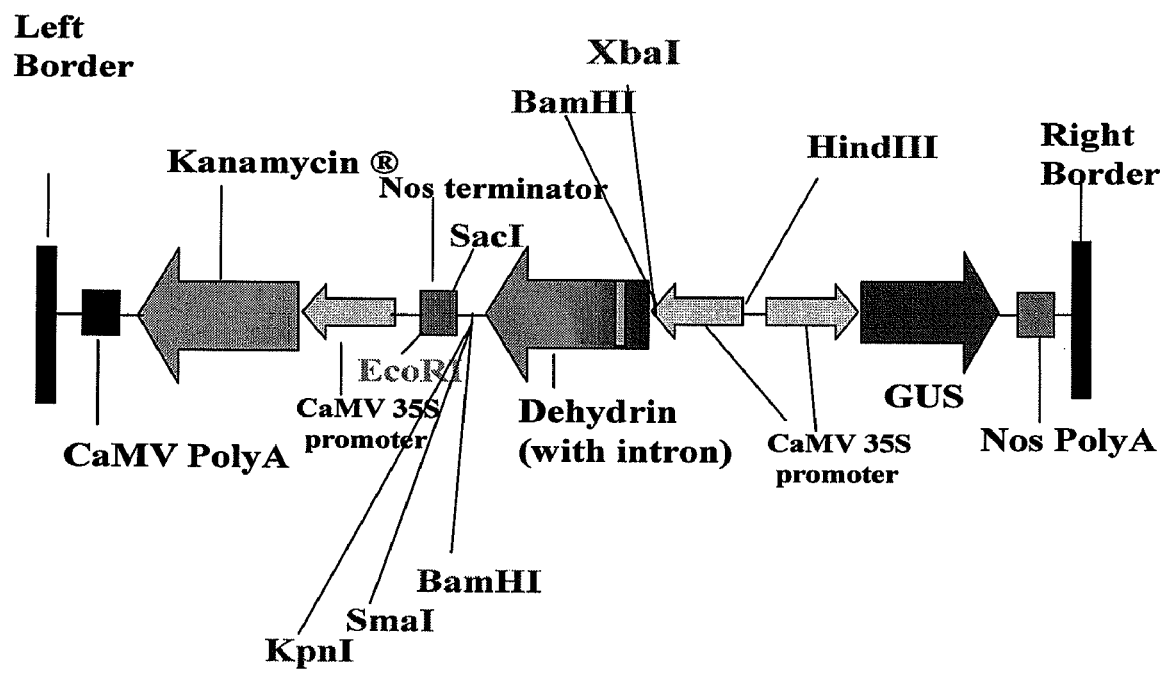
FIG. 2: Depicts a map of pMADY1 which is a diagrammatic representation of recombinant vector pMADY1.

Still another embodiment, the present invention relates to expressing the *A. marina* dehydrin into tobacco (*Nicotiana tobacum*) cv. Wisconsin. The dehydrin gene cloned in pBluescript SK vector designated as AmDHN at the Pst I (5')/Hind III (3') sites was cut with Bam HI and ligated in plant transformation linearized vector pCAMBIA 2301. The resulting recombinant vector is designated as pMADY1. The recombinant vector pMADY1 has the CaMV 35S promoter driving the expression of AmDHN dehydrin gene (SEQ ID NO: 1). The diagrammatic representation of the vector pMADY1 is shown in FIG. 2. This construct, pMADY1, was then mobilized into *Agrobacterium tumefaciens* strain EHA105 by freeze thaw, see Example 6 for details.

In yet another embodiment, the present invention relates to *Agrobacterium* mediated transformation of tobacco using the standard protocol. Sterile tobacco leaf discs were co-cultivated *Agrobacterium* strain harboring AmDHN, which is also the preferred method for tobacco transformation. The alternative ways for plant transformation may involve biolistic method wherein gold or tungsten micro-particles are coated with the plasmid meant to be integrated into the genome and bombarded onto plant tissue. Other plant transformation techniques well known to the person skilled in art include electroporation, micro-injection, poly-ethylene glycol method. The rooted plants were transferred to the soil and grown till maturity. The details of the procedure are provided in Example 7. Transformed plants were confirmed by β-glucouronidase (GUS) staining of stem, leaf and root sections of the plant. The protocol for GUS staining was according to Jefferson R A et al., 1987 (see Example 8). The confirmation was also carried out using standard protocols such as PCR analysis and Southern hybridization, isozyme analysis.

In another embodiment, the present invention provides a promoter sequence corresponding to AmDHN gene. Flanking regions of genes containing these elements are conventionally isolated by screening genomic libraries using cDNA as a probe. However the screening of genomic libraries is a time consuming process. TAIL PCR is a rapid and efficient method for genomic walking. Methods known in the art can be used for the isolation of the promoter sequence. The promoter for dehydrin gene from *A. marina* was isolated using standard TAIL-PCR protocol (Liu and Whittier, 1995). For TAIL PCR, total genomic DNA was extracted. Gene specific primers are designed and used in combination with degenerate primers. For details refer Example 9.

Three gene specific nested primers were designed close to the 5' end. The primers ranged from 23-26 nucleotides in length and had a Tm of 69° C.

The nested gene specific primers that were used are:

```
TR1: 5'-TACGGTGGTGCCGGTGGTTCCAT-3'       SEQ ID NO: 7

TR2: 5'-TGGGATTGCCATACTCGTCGGTCT-3'      SEQ ID NO: 8

TR3: 5'-CTCTGCCATATTCTCTGAGCTTAAAG-3'    SEQ ID NO 9
```

The following arbitrary degenerate primers were used:

```
AD1:    5'-NGTCGASWGANAWGAA-3'      SEQ ID NO: 10

AD2:    5'-TGWGNAGSANCASAGA-3'      SEQ ID NO: 11

AD3:    5'-WGTGNAGWANCANAGA-3'      SEQ ID NO: 12

AD4:    5'-STTGNTASTNCTNTGC-3'      SEQ ID NO: 13
```

The primers AD1, AD2, AD3 and AD4 have following melting temperatures: 46° C., 34° C., 34° C. and 45° C., respectively. A second set of nested gene specific primers were designed from the 750 base pair promoter fragment and these include:

PROMR1: 5'-GGAGAGATATGACACTTGTCGA-3' SEQ ID NO: 14

PROMR2: 5'-GTCGGTTGCAAGACAAGTTAAG-3' SEQ ID NO: 15

PROMR3: 5'-CACCCACTATGAATGTATCATTG-3' SEQ ID NO: 16

One embodiment provides the mRNA from *A. marina* enriched from the total RNA population using streptavidin paramagnetic particles and biotin labeled oligo d(T)$_{18}$ primer. 250 μg total RNA in 10 mM Tris Cl, pH 7.5; 0.5M KCl (Buffer A) was heated to 65° C. with 200 ng biotin labeled oligo d(T) primer and chilled on ice. Biotin-captured mRNA was immobilized by incubation with streptavidin paramagnetic bead suspension (equilibrated in Buffer A). The beads were washed with 10 mM TrisCl, pH 7.5; 0.25 M KCl and the mRNA eluted in DEPC water and concentrated by lyophilization. The concentration and integrity of the eluted mRNA was checked on a 1.2% formaldehyde-agarose gel (Sambrook et al. 1989).

Yet another embodiment of the present invention is directed to analyzing the salt tolerance conferred by overexpressing DHN in *A. marina* transgenics through leaf disc assays (see Example 10).

Yet another embodiment of the present invention is directed to analyzing the salt tolerance conferred by overexpressing DHN in *A. marina* transgenics by performing whole plant salt stress treatments (see Example 10).

Although the foregoing invention has been described in detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are put forth so as to provide those of ordinary skill in the art with a complete disclosure and the description of how to make and use the present invention, and are not intended to limit the scope of what the inventors regard as there invention nor are they intended to represent that the experiments below are all and only experiments performed. Efforts have been made to ensure accuracy with respect to figures used.

Example 1

Plant Growth Conditions and RNA Extraction

*A. marina* seeds were collected from their natural mangrove habitat Pichavaram, Tamil Nadu, India. Seeds were grown in sand-filled trays in the green house at 37° C. and 12 h light/dark photoperiod (illuminated from 6 h to 18 h) in near-submergence conditions and watered daily.

For constructing a cDNA library, one-month-old *A. marina* seedlings (four-leaf stage) were acclimatized for 72 hours in 0.5× Murashige Skoog (MS) medium (no pH adjustment). Subsequently the plants were transferred to 0.5×MS medium supplemented with 0.5M NaCl for 48 hours.

For studying the kinetics of induction of AmDHN, one month old *A. marina* seedlings were acclimatized for 72 hours in 0.5×MS nutrient solution and then exposed to salt stress, osmotic stress and ABA treatment. Root and leaf tissue were frozen separately for total RNA isolation.

Salt stress: Plants (*A. marina*) were stressed with 0.5×MS containing 0.5M NaCl and leaf and root tissue frozen at 6 h, 12 h, 24 h, 48 h NaCl treatment and 12 h and 24 h after salt withdrawal.

Osmotic stress: Plants were stressed with 0.5×MS containing 800 mM mannitol and leaf and root tissue frozen at 12 h, 24 h, 48 h NaCl treatment and 12 h and 24 h after mannitol withdrawal.

ABA treatment: Plants were stressed with 0.5×MS containing 100 μM ABA and leaf and root tissue frozen at 6 h, 12 h, 24 h, 48 h NaCl treatment and 12 h and 24 h after ABA withdrawal.

For RT-PCRs, RNA was isolated from roots of *A. marina* exposed to 12 h of 0.5 M NaCl stress.

Leaf tissue was harvested and total RNA was isolated according to the method given by Chomczynski and Sacchi, 1987. Leaf tissue was harvested from pooled plants and five grams of tissue was macerated in liquid nitrogen and suspended in 18 ml of RNA extraction buffer. To the slurry, 1.8 ml of 2 M sodium acetate (pH 4.0), 18 ml of water saturated phenol and 3.6 ml of 49:1 chloroform:isoamyl alcohol were sequentially added and mixed by inversion. The contents were mixed and cooled on ice for 15 minutes. Finally, the suspension was centrifuged at 10,000×g for 10 minutes at 4° C. After centrifugation, the aqueous phase was transferred to a fresh tube and mixed with equal volume of ice-cold isopropanol and incubated at −20° C. for 1 hour. The samples were centrifuged at 10,000×g for 20 minutes at 4° C. and the pellet was dissolved in 5 ml of RNA extraction buffer. The RNA was again re-precipitated with equal volume of ice-cold isopropanol. The pellet was washed in 70% ethanol and finally dissolved in DEPC water. Purity of the RNA preparation was checked spectrophotometrically by measuring A260/A280 ratio. An A260/A280 value between 1.8 and 2.0 suggested that the RNA was intact and pure. Finally, the total RNA in the samples was estimated by measuring A260. Poly(A$^+$) mRNA was isolated by affinity chromatography on oligo (dT)-cellulose as described by Sambrook et al. (1989).

Example 2

Construction of cDNA Library

The cDNA prepared from poly (A+) mRNA (Superscript Lambda System, Invitrogen) was size fractionated over SizeSep-400 spun column (Amersham-Pharmacia Biotech) and directionally cloned in the Sal I (5')/Not I (3') sites of pSPORT1. The ligated cDNA library was transformed into *E. coli* DH5α. A library of approximately 10$^5$ recombinants was obtained. Plasmid DNA from randomly selected clones was extracted by alkaline lysis method (Feliciello and Chinali 1993). Plasmid DNA was isolated from *E. coli* culture of 3 ml by alkaline lysis method. The cells were harvested in microfuge tubes. The pellet was dissolved in 100 μl of TEG solution [25 mM Tris-HCl (pH 8.0), 10 mM EDTA (pH 8.0) and 50 mM glucose] and left on ice for 20 min. Subsequently, 200 μl of lysis buffer (0.2M NaOH and 1% SDS, freshly prepared) was added to it, mixed well and left on ice for 20 min. To the lysate, 150 μl of 3M potassium acetate (pH 5.2) was added, mixed gently by inversion and left on ice for 20 min. The sample was centrifuged at 10,000 g for 10 min. The supernatant was taken and 2 μl RNAse A (10 mg/ml) was added and incubated at 37° C. for 1 h. The supernatant was mixed with equal volume of phenol:chloroform (1:1 v/v) and centrifuged at 10,000 g for 10 min. The aqueous phase was mixed and transferred to a fresh tube containing equal volume of chloroform and centrifuged at 10,000 g for 10 min. The aqueous phase was transferred to a fresh tube and mixed with 2.5 volumes of ice cold ethanol and left at −20° C. for precipitation for 1 h. The sample was centrifuged at 10,000 g for 10 min and the pellet was washed in 70% ethanol, air-dried and dissolved in 50 µl TE buffer.

Example 3

Sequence Analysis of AmDHN

The complete nucleic acid sequence of both strands of the full length cDNA was determined using the dideoxy chain termination method (Sanger et al., 1977) with an ABI 310 automated DNA sequencer (Perkin-Elmer) using M13/pUC18 forward and reverse primers (SEQ ID NO: 5 and SEQ ID NO: 6) Fifty clones were used in this study for further analysis. From the selected cDNA clone, the cDNA insert was subcloned into pBluescript SK vector at the Pst I (5')/Hind III (3') sites. This recombinant clone is designated as pDHN1. The insert in pDHN1 was sequenced confirmed. The complete coding region was isolated by one-step reverse transciptase-polymerase chain reaction from messenger RNA (mRNA) isolated from roots of A. marina exposed to 12 h of 0.5M NaCl stress. The primers PC57 FWD 2 (SEQ ID NO: 5) and PC57 REV1 (SEQ ID NO: 6) were used. Following PCR conditions (50° C. for 30 min, denaturation at 94° C. for 2 min) followed by 35 cycles (94° C., 1 min; 50° C., 1 min; 72° C., 1 min) followed by 72° C. for 7 minutes in a 9700 DNA thermal cycle apparatus (Perkin-Elmer) were employed. The RT-PCR product was found to be 588 base pairs in length (SEQ ID NO: 2) and encodes for 195 amino acids (SEQ ID NO: 3). This recombinant clone is designated as pDHN2

Example 4

Construction of Protein Expression Vector

The cDNA of AmDHN (was amplified using Taq polymerase and gene-specific primers containing Xba I site: termed as PC57FWD2 (SEQ ID NO: 5) and Xho I termed PC57REV1 (SEQ ID NO: 6) restriction sites. The amplified fragment was digested with Xba I/Xho I and ligated into the Nhe I/Xho I sites of vector pET28a E. coli expression vector (Novagen, Madison, Wis.). The cloned insert was confirmed by automated DNA sequencing using the universal primers. The resulting recombinant vector pET28aDHN was introduced into E. coli BL21 (DE3) pLysS cells using standard procedures well known in the art. The recombinant cells containing plasmid pET28a:DHN were grown in Luria Bertrani medium under kanamycin selection (50 µg/ml) at 220 rpm and 37° C. Recombinant AmDHN expression was induced by adding IPTG to a final concentration of 1 mM when cells reached an OD600 of 0.5. Cells were harvested after 3 hours of induction. Expression of the recombinant protein AmDHN was confirmed by 12% (w/v) SDS-PAGE. The size of the protein is 23.6 kDa.

Example 5

Protein Extraction and Western

Leaves of seedlings were frozen in liquid nitrogen and homogenized (1:5 w/v) in Tris-HCl buffer (100 mM, pH 7.5) containing 2 mM PMSF, 10% glycerol, 5 mM DTT, 1 mM EDTA at 4° C. and centrifuged at 7000×g for 10 min at 4° C. Supernatant was collected and used for further experiments. Total protein extract was quantified by Bradford's dye binding technique using bovine serum albumin as a standard. 80 µg total protein was separated by 12% SDS gel and transferred to a nitrocellulose membrane. Non-specific binding sites were blocked using 3% nonfat dry milk in Tris-buffered saline (TBS) plus Tween 20 for 1 h at room temperature. The nitrocellulose membrane was incubated for 1 h at room temperature with primary antibody (raised polyclonal E. coli anti-dehydrin) and washed in TBS before it was incubated with goat anti-rabbit IgG alkaline phosphatase conjugate (1:1000 dilution with nonfat dry milk in TBS) for 1 h. The second antibody was detected using nitroblue-tetrazolium chloride (NBT) and 5-bromo-4-chloro-3-indolyl-phosphate (BCIP).

Example 6

Construction of Plant Transformation Vector

To express the A. marina dehydrin into tobacco (Nicotiana tobacum) cv. Wisconsin, the cDNA cloned in pBluescript SK vector designated as AmDHN at the Pst I (5')/Hind III (3') sites was cut with Bam HI and ligated in plant transformation vector pCAMBIA 2301 linearized. The resulting recombinant vector is designated as pMADY1. The recombinant vector pMADY1 has the CaMV 35S promoter driving the expression of AmDHN dehydrin gene with intron (SEQ ID NO: 1). The diagrammatic representation of the vector pMADY1 is shown in FIG. 3. This construct, pMADY1, was then mobilized into Agrobacterium tumefaciens strain EHA105 by freeze thaw method.

Example 7

Tobacco Transformation

Agrobacterium mediated transformation of tobacco was carried out using the standard protocol. Sterile tobacco leaf discs were cut and transferred to Murashige and Skoog (MS) medium containing 3% sucrose, 1 mg/l BAP, 1 mg/l NAA, 0.8% bacto-agar, pH 5.6 at 28° C. in 16 hours light and 8 hours darkness for 24 hours prior to transformation. Hundred mL of an overnight grown culture of transformed Agrobacterium strain was re-suspended in 0.5×MS liquid medium with 3% sucrose, pH 5.6 (5 ml). The leaf discs were subsequently co-cultivated with the re-suspended AmDHN transformed Agrobacterium for 30 minutes. The discs were dried on sterile No. 1 Whatmann discs and transferred to MS medium containing 3% sucrose, 1 mg/l BAP, 1 mg/l NAA, and 0.8% bacto-agar, pH 5.6 at 28° C. in 16 hours light and 8 hours darkness for 48 hrs. The leaf discs were given several washes in liquid MS medium with 3% sucrose, pH 5.6 containing 250 mg/ml cefotaxime. Excess moisture on the leaf discs was blotted on sterile Whatmann No. 1 filter paper. The discs were then placed on selection media, that is, MS medium containing 3% sucrose, 1 mg/l BAP, 1 mg/l NAA, 0.8% bacto-agar, pH 5.6 containing 250 mg/ml cefotaxime and 50 mg/l kanamycin at 28° C. in 16 hours light and 8 hours darkness. The leaf discs were transferred to fresh selection media every 14 days until multiple shoot regeneration was seen. Shoot regeneration was seen between 20-35 days after first placing on the selection media. Independent shoots were then transferred to rooting medium (MS medium containing 3% sucrose, 0.8% bacto-agar, pH 5.6 containing 250 mg/ml cefotaxime and 50 mg/l kanamycin at 28° C. (in 16 hours light and 8 hours darkness). After establishment of roots in the medium the plants transferred to fresh rooting medium every 14 days, each time transferring a shoot cut from the previous plant. The rooted plants were transferred to the soil and grown till maturity. A total of twenty five transformed plants were obtained using the vector pMADY1.

Example 8

Confirmation of Transformed Plants

Transformed plants were confirmed by β-glucouronidase (GUS) staining of stem, leaf and root sections of the plant. The protocol for GUS staining was according to Jefferson R A et al., 1987. The confirmation was also carried out using standard protocols such as PCR analysis and Southern hybridization, isozyme analysis.

Example 9

Isolation of AmDHN Promoter Through TAIL PCR

For TAIL PCR, total genomic DNA was extracted using standard protocol. The gene specific primers are designed and used in combination with degenerate primers. For primary reaction *Avicennia marina* genomic DNA was used as template. Two successive rounds of PCR were carried out using the products of previous PCR as templates, employing a common arbitrary primer and a gene specific primer in a consecutive manner. The products of the primary, secondary and tertiary reactions were separated on adjacent lanes in a 1.5% agarose gel, and discrete PCR products, showing difference in size corresponding to the relative positions of the gene specific primers were identified. Three gene specific nested primers were designed close to the 5' end. The primers ranged from 23-26 nucleotides in length and had a Tm of 69° C. The nucleotide sequence of the nested gene specific primers that were used are shown in SEQ ID NO: 7, SEQ ID NO: 8 and SEQ ID NO: 9

The nucleotide sequence of the arbitrary degenerate primers that were used is as shown in SEQ ID NO: 10, SEQ ID NO: 11, SEQ ID NO: 12 and SEQ ID NO: 13.

The primers AD1 (SEQ ID NO: 10), AD2 (SEQ ID NO: 11), AD3 (SEQ ID NO: 12) and AD4 (SEQ ID NO: 13) have following melting temperatures: 46° C., 34° C., 34° C. and 45° C., respectively. A second set of nested gene specific primers were designed from the 750 base pair promoter fragment and these include: PROMR1 (SEQ ID NO: 14), PROMR2 (SEQ ID NO: 15) and PROMR3 (SEQ ID NO: 16).

The second set of primers range from 22-23 nucleotides in length with a melting temperature of 59° C. The second promoter fragment was 55 base pairs in length. The total promoter length was 843 bp. Each primary reaction mixture (20 µl) comprises of, 2.5 µl 10×PCR buffer, 200 µM each of dNTPs, 0.2 µM gene specific primer and 2 µM of any one of the AD primers, 1 unit of Taq DNA polymerase and 25 ng genomic DNA. Primary amplification with thermal conditions was performed as summarized in Table 1. Secondary PCR mixtures (25 µl) containing the same components were prepared. One microlitre of the primary PCR product was diluted with 39 µl distilled water and 1 µl of the diluted DNA was added to the secondary PCR mixture. Secondary amplification with thermal conditions was performed as summarized in Table 1. Tertiary PCR mixtures (25 µl) containing the same components were prepared. One microlitre of the secondary PCR product was diluted with 9 µl of distilled water and 1 µl of this diluted DNA was added to the tertiary PCR mixture. Amplified products from the reactions with TR1, TR2 and TR3 were analyzed with agarose gel electrophoresis and a difference in product size consistent with primer positions was used as a criterion. The correct size fragment was re-amplified, gel-eluted and ligated to the TA vector. Plasmid isolation was carried out for the corresponding bacterial colony and this DNA was used as a template for DNA sequencing.

Example 10

Salt Stress Analysis in Transgenic Tobacco Plants

Leaf-disc assays with NaCl solution:

Twenty-six leaf-discs from control and transgenic plants were floated on 100 mM NaCl solution and H₂O (water control) for this experiment. The percent chlorophyll loss was estimated for control and transgenic plants. Control leaf-discs showed a visible damage in NaCl. It was found that control plants showed 70% chlorophyll loss while transgenic plants showed 39% less chlorophyll loss.

Whole-Plant Salt Stress Treatments:

The salt tolerance conferred by over-expressing DHN in *A. marina* transgenics was analyzed by performing whole plant salt stress treatments. Phenotypic growth retardation study was also performed between control and transgenic plants. Transgenic plants were grown along with control initially in ½ MS for 1 week. Later, they were transferred to ½ MS medium supplemented with 150 mM and 200 mM NaCl. It was observed that in 150 mM NaCl, transgenic plants showed better rooting when compared to control plants. At 200 mM NaCl, both control and transgenic plants did not root. It was also found that the transgenic plants suffered less damage in 150 mM and 200 mM NaCl stress. Phenotypic growth retardation was not evident in control and transgenic plants grown in pots and irrigated with 150 mM NaCl solution for 1½ week. The plants showed increased salt tolerance.

---

We claim:

1. An isolated polynucleotide comprising a polynucleotide sequence having at least 80% similarity to SEQ ID NO: 1 and coding for a dehydrin polypeptide having the amino acid sequence as shown in SEQ ID NO: 3.

2. An isolated polynucleotide comprising the polynucleotide sequence as set forth in SEQ ID NO: 1 and coding for a dehydrin polypeptide having the amino acid sequence as shown in SEQ ID NO: 3.

3. A recombinant construct for transforming plants to confer salt stress tolerance comprising a promoter selected from the group consisting of 35S CaMV, nopaline synthase, OCS, AdhI, AdhII and Ubi-1, wherein the promoter is operably linked to a polynucleotide comprising a polynucleotide sequence having at least 80% similarity to SEQ ID NO: 1 and coding for a dehydrin polypeptide having the amino acid sequence as shown in SEQ ID NO: 3.

4. A method of transformation of plants to confer salt stress tolerance, said method comprising transforming plants with a recombinant vector comprising a promoter operably linked to a polynucleotide comprising a polynucleotide sequence having at least 80% similarity to SEQ ID NO: 1 and coding for a dehydrin polypeptide having the amino acid sequence as shown in SEQ ID NO: 3, and wherein expression of the polynucleotide confers tolerance to salt stress in said plants.

5. The method as claimed in claim 4, wherein the transformation is carried out by a method selected from the group consisting of *Agrobacterium*-mediated transformation, particle gun bombardment, vacuum-infiltration, in planta transformation and chemical methods.

6. A method of transforming plants, wherein the method comprises:
   (a) constructing a recombinant construct comprising a promoter selected from the group consisting of 35S CaMV, nopaline synthase, OCS, AdhI, AdhII and Ubi-1, wherein the promoter is operably linked to a polynucleotide comprising a polynucleotide sequence having at least 80% similarity to SEQ ID NO: 1 and coding for a dehydrin polypeptide having the amino acid sequence as shown in SEQ ID NO: 3,
   (b) mobilizing the recombinant construct into *Agrobacterium* strain to produce recombinant *Agrobacterium* strain,
   (c) obtaining an explant from the plant,
   (d) cultivating the explant with the recombinant *Agrobacterium* strain to produce transformed plant cells, and
   (e) culturing the transformed plant cells to produce transformed plants.

7. The method as claimed in claim 6, wherein said plant is either a monocotyledonous or a dicotyledonous plant.

8. The method as claimed in claim 7, wherein the monocotyledonous plant is selected from the group consisting of rice, maize, wheat, barley and sorghum.

9. The method as claimed in claim 7, wherein the dicotyledonous plant is selected from the group consisting of tobacco, tomato, pea, soybean, *brassicas*, peanut, chickpea and pigeon pea.

10. The method as claimed in claim 6, wherein *Agrobacterium* is selected from the group consisting of LBA4404, EHA101 and EHA105.

11. The method as claimed in claim 6, wherein the explant is selected from the group consisting of leaf, stem, root, hypocotyl and embryo.

12. A transgenic plant transformed with a polynucleotide comprising a polynucleotide sequence having at least 80% similarity to SEQ ID NO: 1 and coding for a dehydrin polypeptide having the amino acid sequence as shown in SEQ ID NO: 3.

13. The transgenic plant as claimed in claim 12, wherein said plant is selected from the group consisting of tobacco, tomato, pea, soybean, *Brassica*, chickpea, pigeon pea, rice, maize, wheat, barley and sorghum.

14. A plant, a plant part, a seed, a plant cell or a progeny thereof, wherein the plant, plant part, seed, plant cell, or progeny thereof comprises the recombinant construct as claimed in claim 3.

* * * * *